US007422368B2

(12) United States Patent
Stayman et al.

(10) Patent No.: US 7,422,368 B2
(45) Date of Patent: Sep. 9, 2008

(54) CT SCANNER WITH TRIPOD BASE

(75) Inventors: Joseph Webster Stayman, Ann Arbor, MI (US); David C. Brown, Chicago, IL (US); Wai Ngai Chin, Glenview, IL (US); James F. O'Connell, Ann Arbor, MI (US); James A. Bertolina, Portage, MI (US); Dejen Teofilovic, Ann Arbor, MI (US)

(73) Assignee: Xoran Technologies, Inc., Ann Arbor, MI (US)

( * ) Notice: Subject to any disclaimer, the term of this patent is extended or adjusted under 35 U.S.C. 154(b) by 76 days.

(21) Appl. No.: 11/546,933

(22) Filed: Oct. 12, 2006

(65) Prior Publication Data
US 2008/0095323 A1 Apr. 24, 2008

(51) Int. Cl.
*H05G 1/02* (2006.01)
(52) U.S. Cl. .......................................... 378/198; 378/4
(58) Field of Classification Search ............... 378/4–20, 378/102, 195–198, 210, 193
See application file for complete search history.

(56) References Cited

U.S. PATENT DOCUMENTS

| 5,873,586 A * | 2/1999 | Krimmell ............ 280/124.113 |
| 2004/0042587 A1* | 3/2004 | Deshpande .................. 378/198 |
| 2004/0170254 A1* | 9/2004 | Gregerson et al. .......... 378/197 |
| 2004/0210126 A1* | 10/2004 | Hajaj et al. .................. 600/407 |
| 2006/0083354 A1* | 4/2006 | Tybinkowski et al. ....... 378/198 |

* cited by examiner

*Primary Examiner*—Hoon Song
(74) *Attorney, Agent, or Firm*—Carlson, Gaskey & Olds

(57) ABSTRACT

A CT scanner includes a base, two fixed portions extending transversely from the base, and a rocking beam pivotally attached to the base about an axis. The CT scanner includes four wheels that allow the CT scanner to move over a floor. A wheel is attached to each fixed portion, and a wheel is attached to each end of the rocking beam. If the CT scanner is positioned on a floor with an unlevel portion, the rocking beam rotates about the axis. One wheel attached to the rocking beam raises in a generally vertical direction, and the other beam attached to the rocking beam lowers in a generally vertical direction so all four wheels contact the floor, stabilizing the CT scanner and preventing rocking.

24 Claims, 7 Drawing Sheets

CT SCANNER WITH TRIPOD BASE

STATEMENT REGARDING FEDERALLY SPONSORED RESEARCH OR DEVELOPMENT

This invention was made with government support under grant number R44CA107895, awarded by the National Institute of Health (NIH). The government has certain rights in the invention.

BACKGROUND OF THE INVENTION

The present invention relates generally to a CT scanner including a tripod base that increases stability of the CT scanner on an unlevel floor.

A prior art CT scanner takes a plurality of x-ray images of a part of a patient to create a three-dimensional CT image. The CT scanner includes a base having four wheels that allow the CT scanner to move on a floor. In a generally vertical direction, a distance between a top of each of the wheels and the base is constant and equal. That is, the wheels are fixed and do not move in a generally vertical direction.

If a concrete floor is not evenly poured, the floor may not be level. As a result, one of the wheels of the CT scanner may not contact the floor. If this occurs, the CT scanner could rock and move during a CT scan, affecting the resulting three-dimensional CT image. Another CT scan would need to be taken, exposing the patient to additional x-rays.

Hence, there is a need in the art for a CT scanner including a tripod base that increases the stability of the CT scanner on an unlevel floor.

SUMMARY OF THE INVENTION

A CT scanner includes a gantry that supports and houses components of the CT scanner. The gantry includes a cross-bar section, and a first arm and a second arm each extend substantially perpendicularly from opposing ends of the cross-bar section. The first arm houses an x-ray source that generate x-rays. The second arm houses a complementary flat-panel detector. The x-rays are directed towards the detector which includes a converter that converts the x-rays from the x-ray source to visible light and an array of photodetectors behind the converter to create an image. As the gantry rotates about the patient, the detector takes a plurality of x-ray images at a plurality of rotational positions to create a three-dimensional CT image.

The CT scanner includes a base. Two fixed arms extend transversely from a rear area of the base. A rocking beam is pivotally attached to a front area of the base about a pivot post having an axis.

The CT scanner includes four wheels that allow the CT scanner to move on a floor. A wheel is attached to each fixed arm, and a wheel is attached to each end of the rocking beam. Two bumpers made of an elastic material are positioned between a flange and an upper surface of the rocking beam. As the rocking beam rotates about the axis, the wheels attached to the rocking beam can raise or lower in a generally vertical direction relative to the base.

When the CT scanner is positioned on a level floor, the rocking beam is substantially horizontal, and a distance between a top of each of the four wheels and the base in a generally vertical direction is approximately equal. When the CT scanner is positioned on a floor including an unlevel portion, the rocking beam pivots about the axis, raising one wheel attached to the rocking beam in a generally vertical direction and lowering the other wheel attached to the rocking beam in a generally vertical direction to accommodate for the unlevel floor and prevent rocking of the CT scanner. The wheels attached to the fixed arms do not raise or lower relative to the base. All four wheels contact the floor, providing four points of contact with the floor. However, as the rocking beam pivots about the axis, the CT scanner is balanced on three points of balance with the floor.

These and other features of the present invention will be best understood from the following specification and drawings.

BRIEF DESCRIPTION OF THE DRAWINGS

Other advantages of the present invention can be understood by reference to the following detailed description when considered in connection with the accompanying drawings wherein.

DETAILED DESCRIPTION OF THE PREFERRED EMBODIMENT

Figure 1:
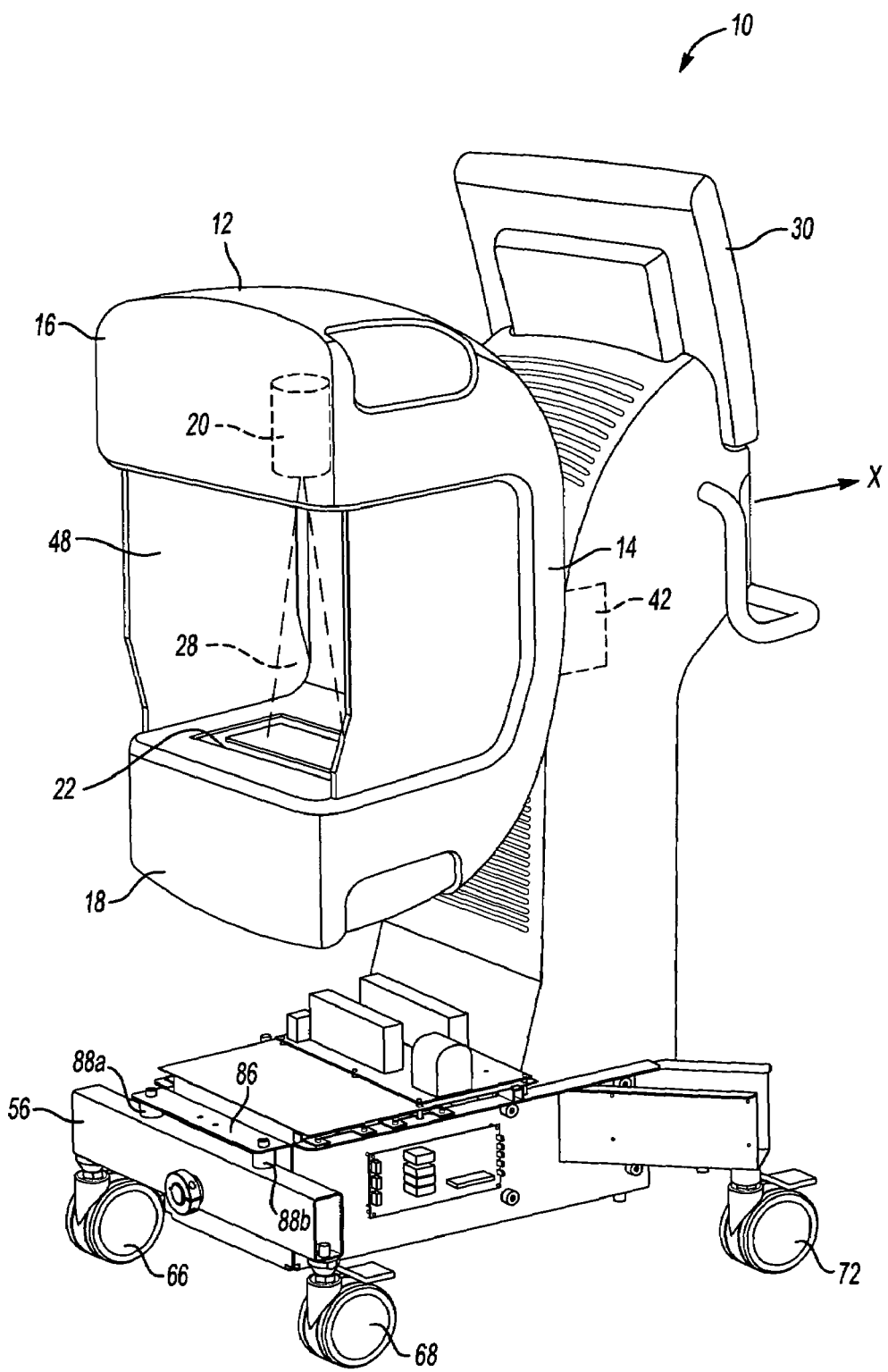
FIG. 1 illustrates a perspective view of a CT scanner of the present invention.

FIG. 1 illustrates a CT scanner 10 of the present invention. The CT scanner 10 includes a gantry 12 that supports and houses components of the CT scanner 10. In one example, the gantry 12 includes a cross-bar section 14, and a first arm 16 and a second arm 18 each extend substantially perpendicularly from opposing ends of the cross-bar section 14 to form the c-shaped gantry 12. The first arm 16 houses an x-ray source 20 that generate x-rays 28. In one example, the x-ray source 20 is a cone-beam x-ray source. The second arm 18 houses a complementary flat-panel detector 22. The x-rays 28 are directed toward the detector 22 which includes a converter (not shown) that converts the x-rays 28 from the x-ray source 20 to visible light and an array of photodetectors behind the converter to create an image. As the gantry 12 rotates about the patient P, the detector 22 takes a plurality of x-ray images at a plurality of rotational positions. Various configurations and types of x-ray sources 20 and detectors 22 can be utilized, and the invention is largely independent of the specific technology used for the CT scanner 10.

Figure 2:
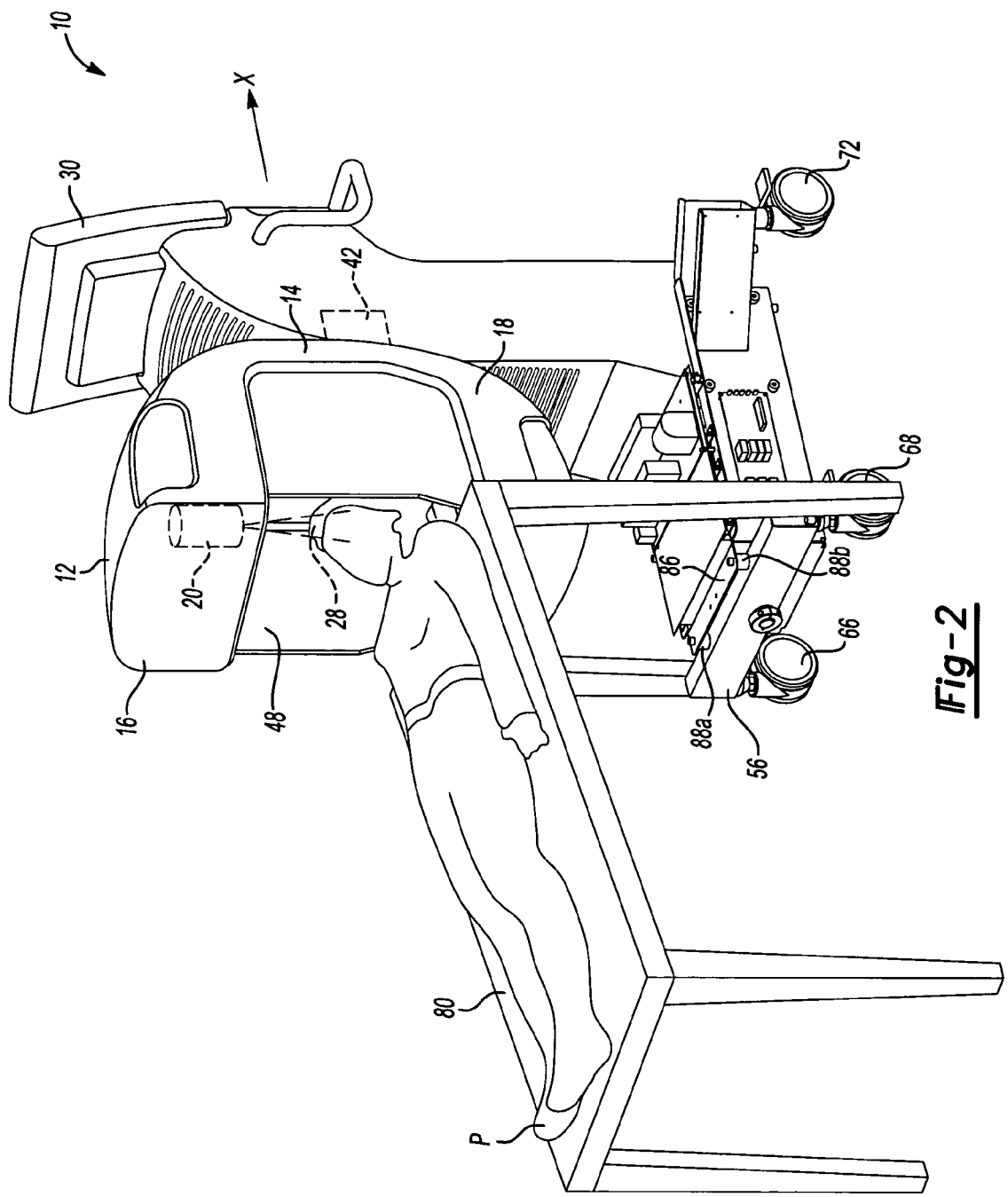
FIG. 2 illustrates the CT scanner of FIG. 1 with a part of a patient received in the CT scanner.

FIG. 2 illustrates the CT scanner 10 with a part of the patient P received in a space 48 between the first arm 16 and the second arm 18. In this example, the patient P is typically lying down on a table 80. A motor 42 rotates the gantry 12 about an axis of rotation X to obtain a plurality of x-ray images of the patient P at the plurality of rotational positions. The axis of rotation X is substantially centered within the gantry 12 and positioned between the x-ray source 20 and the detector 22. The gantry 12 can be rotated approximately slightly more than 360 degrees about the axis of rotation X. In one example, as shown in FIGS. 1 and 2, the axis of rotation X is substantially horizontal.

Figure 3:
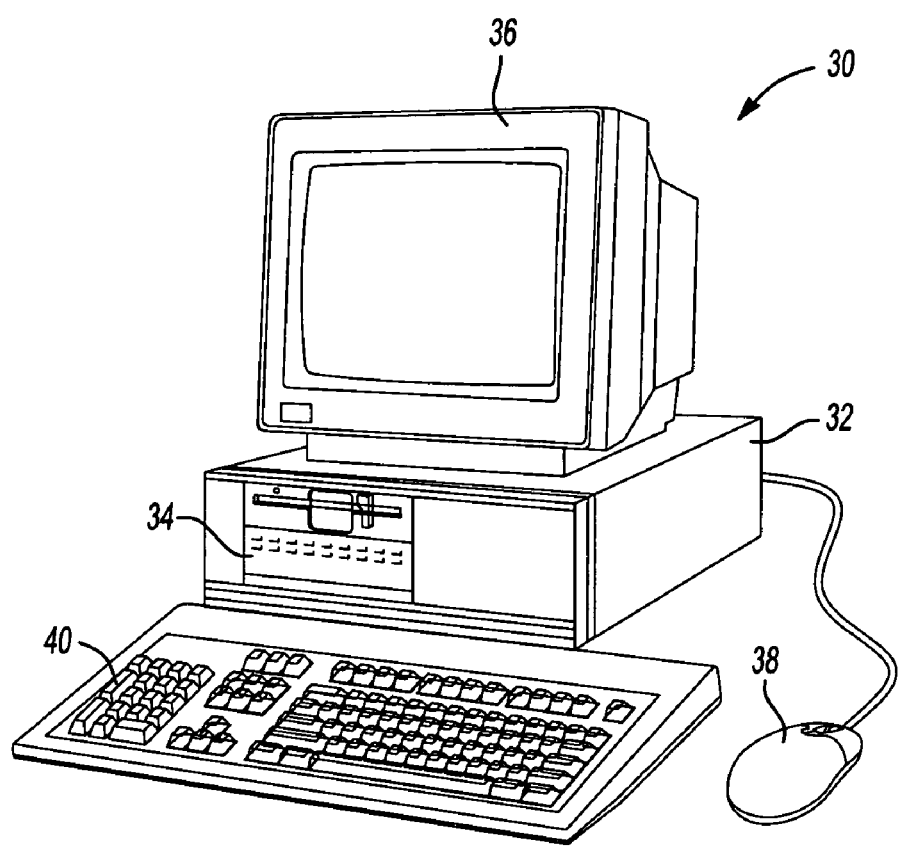
FIG. 3 illustrates a computer employed with the CT scanner of the present invention.

As shown schematically in FIG. 3, the CT scanner 10 further includes a computer 30 having a microprocessor or CPU 32, a storage 34 (memory, hard drive, optical, and/or magnetic, etc), a display 36, a mouse 38, a keyboard 40 and other hardware and software for performing the functions described herein. The computer 30 powers and controls the x-ray source 20 and the motor 42. The plurality of x-ray images taken by the detector 22 are sent to the computer 30. The computer 30 generates a three-dimensional CT image from the plurality of x-ray images utilizing any known techniques and algorithms. The three-dimensional CT image is stored on the storage 34 of the computer 30 and can be displayed on the display 36 for viewing.

Figure 4:
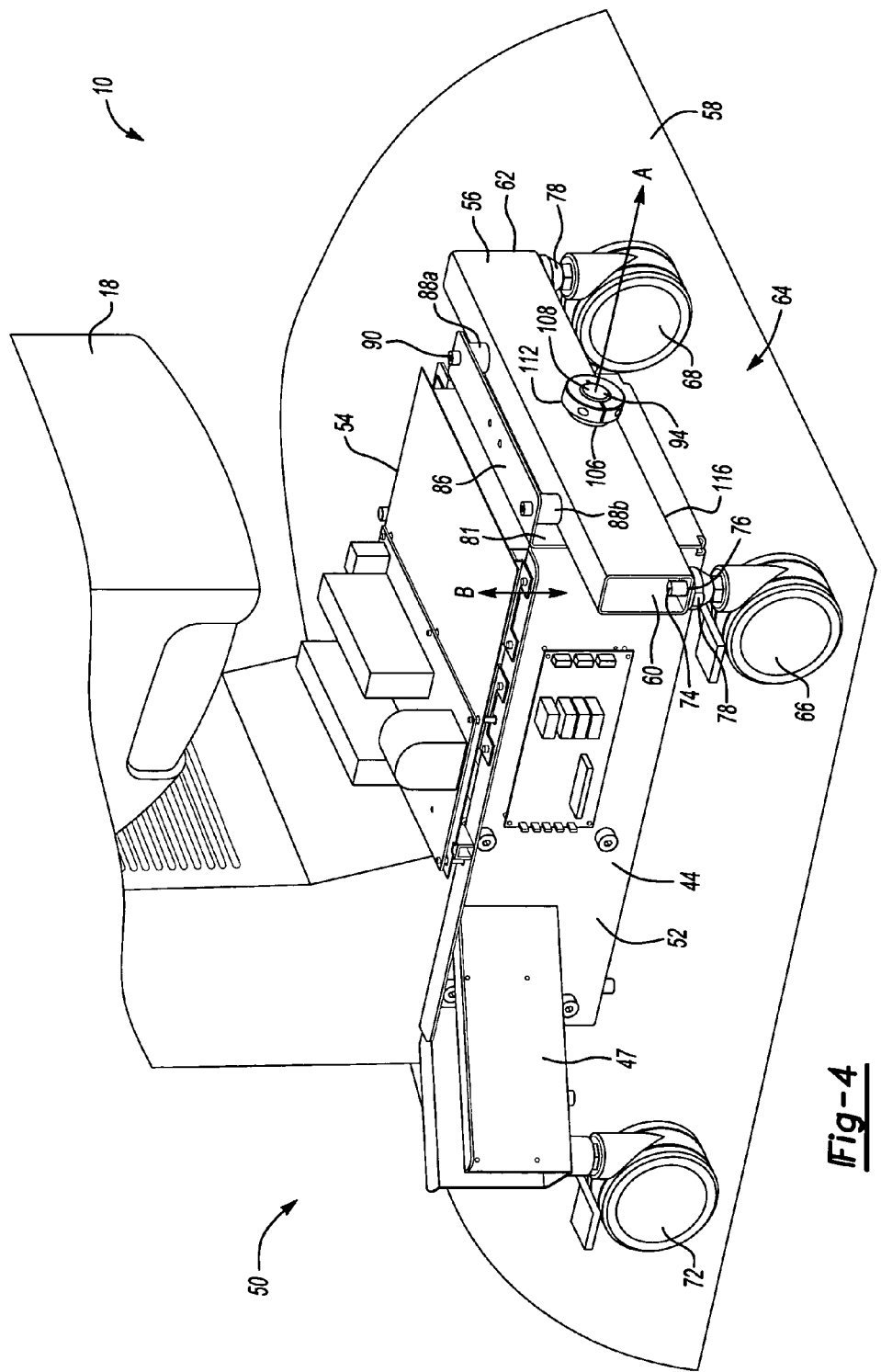
FIG. 4 illustrates is a perspective view of a lower part of the CT scanner.
Figure 5:
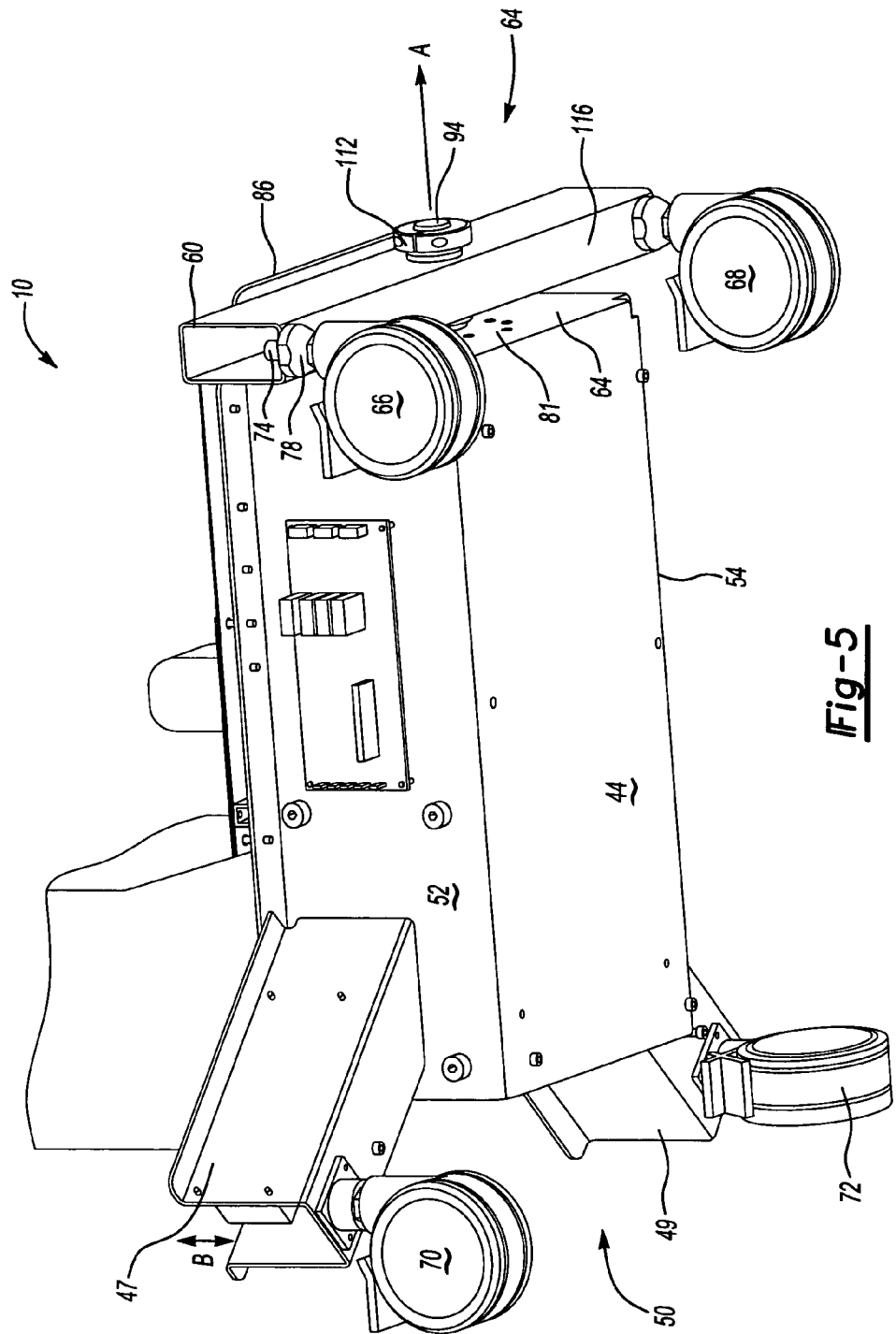
FIG. 5 illustrates a bottom perspective view of the CT scanner.

FIGS. 4 and 5 illustrate a perspective view of the CT scanner 10. The CT scanner 10 includes a base 44. Fixed portions 47 and 49 extend transversely from a rear area 50 of the base 44. The fixed portions 47 and 49 are fixed relative to the base 44 and do not move. In one example, the fixed portions 47 and 49 extend transversely from sides 52 and 54, respectively, of the base 44 near the rear area 50. In one example, the base 44 is substantially rectangular in shape. However, one skilled in the art would understand that other shapes are possible.

The CT scanner 10 also includes a rocking beam 56 pivotally attached to a front area 64 of the base 44 about an axis A. The rocking beam 56 is moveable relative to the base 44 by pivoting about the axis A. The rocking beam 56 includes a first end 60 and an opposing second end 62. When the CT scanner 10 is located on a level floor 58, the rocking beam 56 and the axis A is substantially parallel to a floor 58.

Although it is illustrated and described that the fixed portions 47 and 49 are located at the rear area 50 of the base 44 and the rocking beam 56 is located at the front area 64 of the base 44, it is to be understood that any configuration is possible. For example, the fixed portions 47 and 49 can be located at the front area 64 of the base 44, and the rocking beam can be located at the rear area 50 of the base 44.

The CT scanner 10 includes four wheels 66, 68, 70 and 72 that allow the CT scanner 10 to move over the floor 58. Although four wheels 66, 68, 70 and 72 are illustrated and described, it is to be understood that any number of wheels can be employed. The four wheels 66, 68, 70 and 72 provide four points of contact with the floor 58. The wheel 66 is attached to the rocking beam 56 between the first end 60 and the axis A, and the wheel 68 is attached to the rocking beam 56 between the second end 62 and the axis A. In one example, the wheel 66 is attached near the first end 60, and the wheel 68 is attached near the second end 62. As the rocking beam 56 is rotatable about the axis A, the wheels 66 and 68 attached to the rocking beam 56 move in an arc. The resulting arc movement causes the wheels 66 and 68 to move to a new position that is displaced both horizontally and vertically from the original position. Therefore, when the rocking beam 56 pivots about the axis A, the wheels 66 and 68 raise or lower in a generally vertical direction relative to the base 44. For example, if the first end 60 and the wheel 66 move upwardly, the second end 62 and the wheel 68 move downwardly. Conversely, if the first end 60 and the wheel 66 move downwardly, the second end 62 and the wheel 68 move upwardly.

The wheel 70 is attached to the fixed portion 47, and the wheel 72 is attached to the fixed portion 49. The fixed portions 47 and 49 are fixed relative to the base 44, and therefore, the wheels 70 and 72 do not move in a generally vertical direction relative to the base 44.

An attachment mechanism fixes the wheels 66, 68, 70 and 72 to the fixed portions 47 and 49 or the rocking beam 56, allowing the wheels 66, 68, 70 and 72 to rotate about an axis B. The wheels 66, 68, 70 and 72 can be attached in any known manner. In one example, each wheel 66, 68, 70 and 72 includes a structure 74 that is received in an opening 76 in the fixed portion 47 and 49 or the rocking beam 56. A securing feature 78 secures the structure 74 to the fixed portion 47 and 49 or the rocking beam 56, securing the wheel to the fixed portion 47 and 49 or the rocking beam 56. However, the wheels 66, 68, 70 and 72 can rotate about the axis B. Although FIG. 4 only illustrates these features with respect to the wheel 66, the other wheels 68, 70 and 72 include the same features.

Figure 6:
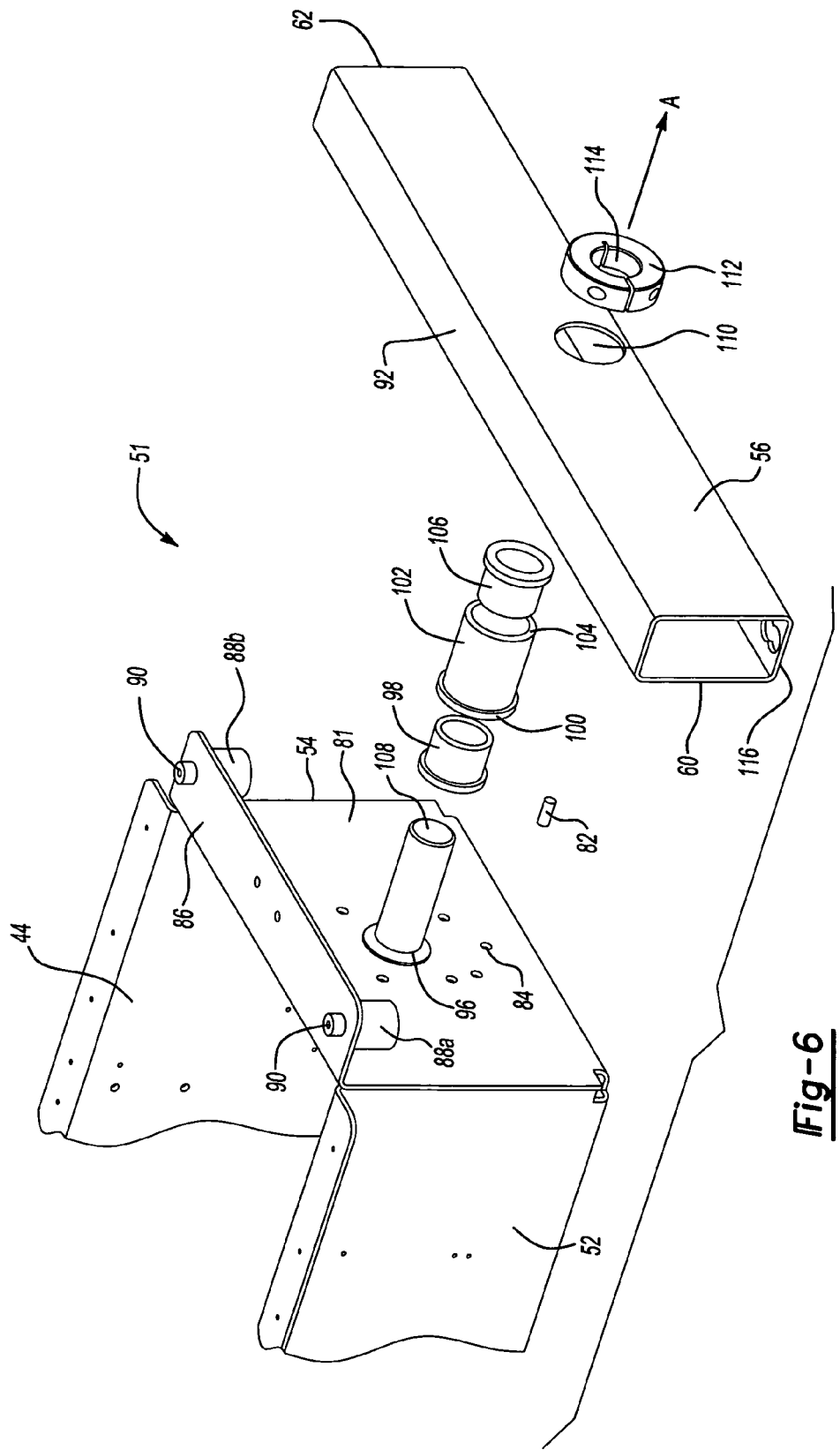
FIG. 6 illustrates an exploded view of a pivoting mechanism of the CT scanner.

FIG. 6 illustrates an exploded view of a pivot mechanism 51 that allows the rocking beam 56 to pivot about the axis A relative to the base 44. A panel 81 it attached to the base 44 by attachment members 82 (only one shown) received in apertures 84 in the panel 81. A flange 86 extends transverse to the panel 81. In one example, the flange 86 is substantially perpendicular to the panel 81. Two bumpers 88a and 88b are attached to the flange 86. The bumpers 88a and 88b are made of an elastic material. In one example, the bumpers 88a and 88b are made of rubber. Each bumper 88a and 88b is attached to the flange 86 with an attachment member 90. The bumpers 88a and 88b are located between the flange 86 and an upper surface 92 of the rocking beam 56. Each bumper 88a and 88b is located between the axis A and one of the first end 60 and the second end 62, respectively, of the rocking beam 56. The amount of pivoting of the rocking beam 56 is limited by the bumpers 88a and 88b and the floor 58.

A pivot post 94 extends from an opening 96 in the panel 81 along the axis A. In one example, the pivot post 94 is substantially perpendicular to the panel 81. A first bushing 98 is received on an end 108 of the pivot post 94. A portion of the first bushing 98 is received in a first end 100 of a connector 102, and a portion of a second bushing 106 is received in a second end 104 of the connector 102. The end 108 of the pivot post 94 with the attached bushings 98 and 106 and the connector 102 are inserted into an opening 110 in the rocking beam 56. A locking ring 112 secures the pivot post 94 to the rocking beam 56, exposing the end 108 of the pivot post 94 through an opening 114 in the locking ring 112. Therefore, the rocking beam 56 is connected to the pivot post 94. Pivotal movement of the pivot post 94 about the axis A causes pivotal movement of the rocking beam 56.

Figure 7:
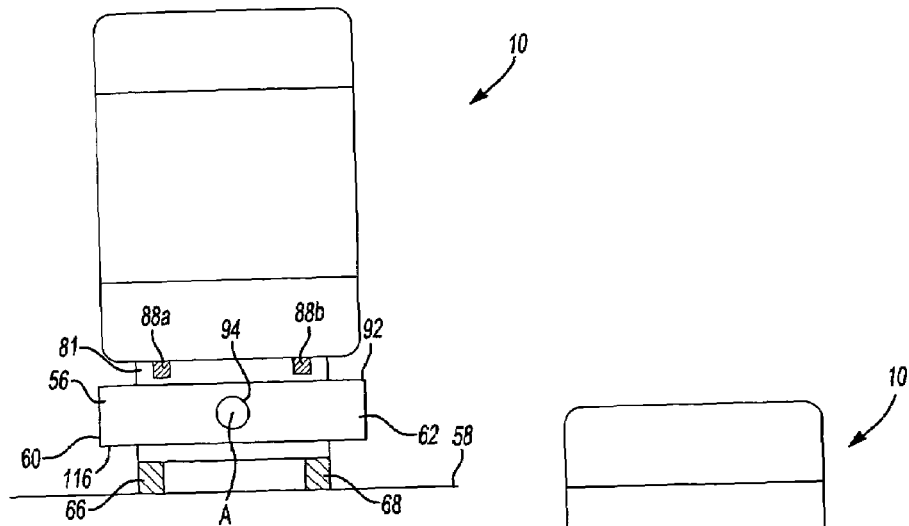
FIG. 7 illustrates a front view of the CT scanner on a level floor.

FIG. 7 illustrates a front view of the CT scanner 10 on a level floor 58. As shown, a bottom surface 116 and the upper surface 92 of the rocking beam 56 are substantially parallel to the floor 58. A top of each of the four wheels 66, 68, 70 and 72 (only wheels 66 and 68 are shown) is located at approximately an equal distance from the bottom surface 116 of the rocking beam 56. When the CT scanner 10 is on a level floor 58, there is a gap between the bumpers 88a and 88b and the upper surface 92 of the rocking beam 56.

Figure 8:
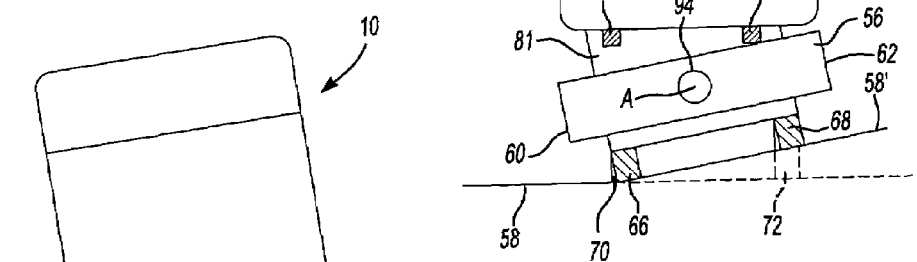
FIG. 8 illustrates a front view of the CT scanner on a floor with an unlevel portion.
Figure 9:
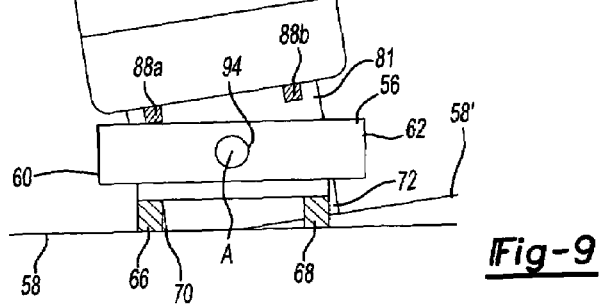
FIG. 9 illustrates another front view of the CT scanner on a floor with an unlevel portion.

FIGS. 8 and 9 illustrate a front view of the CT scanner 10 on a floor 58 including an unlevel portion 58'. The unlevel portion 58' is shown at a larger angle for illustrative purposes only. The rocking beam 56 pivots about the axis A to accommodate for the unlevel portion 58' and to adjust the position of the wheels 66 and 68 so that all the wheels 66, 68, 70 and 72 contact the floor 58. Therefore, the CT scanner 10 has four points of contact with the floor 56. However, the CT scanner is balanced on three points of balance: the wheel 70 defines a first point of balance, the wheel 72 defines a second point of balance, and the axis A defines a third point of balance. In this manner, the CT scanner 10 has a tripod type base. As there are fewer points of balance with the floor 58, the position of the CT scanner 10 can stabilize and not rock when positioned on a floor 58 with an unlevel portion 58'. Once the CT scanner 10 is again positioned on a level floor 58, gravity and the elastic bumpers 88a and 88b bias the rocking beam 56 to the original position.

For example, in FIG. 8, the unlevel portion 58' is located near the front of the CT scanner 10. The wheel 68 is located on a portion of the floor 58 that is raised to provide the unlevel portion 58'. The rocking beam 56 pivots about the axis A to accommodate for the unlevel portion 58' in the floor 58, raising the second end 62 of the rocking beam 56 in a generally vertical direction. The bumper 88b is made of an elastic material, and the second end 62 of the rocking beam 56 slightly compresses the bumper 88b to accommodate for this movement. The movement of the first end 60 of the rocking beam 56 in an arc lowers the wheel 66 generally vertically so the wheel 66 contacts the floor 58. The wheels 70 and 72 are attached to the fixed portion 47 and 49, respectively, and do not move relative to the base 44.

In another example shown in FIG. 9, the unlevel portion 58' is located near the rear of the CT scanner 10. The wheel 72 is located on a portion of the floor 58 that is raised to provide an unlevel portion 58'. In this instance, the entire CT scanner 10 would slightly tilt because the wheel 72 on the unlevel portion 58' is attached to the fixed portion 49 that does not move relative to the base 44. However, the rocking beam 56 pivots about the axis A, lowering the second end 62 of the rocking beam 56 in a generally vertical direction. Therefore, the rocking beam 56 is maintained substantially parallel to the floor 58 and substantially horizontal. The first end 60 of the rocking beam 56 slightly compresses the bumper 88a to accommodate for this movement. The movement of the second end 62 of the rocking beam 56 in an arc lowers the wheel 68 generally vertically so the wheel 68 contacts the floor 58. The wheels 70 and 72 are attached to the fixed portion 47 and 49, respectively, and do not move relative to the base 44.

The wheels 66, 68, 70 and 72 of the CT scanner 10 of the present invention provide four points of contact with the floor 58, but the CT scanner 10 is balanced on three points of balance, providing a tripod base. Therefore, there is increased stability of the CT scanner 10 to prevent rocking when the CT scanner 10 is positioned on a floor 58 with an unlevel portion 58'. That is, the three points of balance provide image stability, while the four points of contact provide ease of mobility and good tip/tilt stability.

Additionally, if the CT scanner 10 is bumped, at some point one of the bumpers 88a and 88b will reach a maximum compression as the rocking beam 56 compresses the affected bumper 88a and 88b. For example, if the CT scanner 10 is bumped on the side 52, the front two wheels 66 and 68 will continue to contact the floor 56 as the bump causes the rocking beam 56 to pivot and compress the bumper 88b. At some point when the bumper 88b reaches a maximum compression, the wheel 68 acts on the base 44 at a point further from the center of gravity of the CT scanner 10 to prevent tipping. Therefore, the CT scanner is stabilized 10 and does not tilt.

The foregoing description is only exemplary of the principles of the invention. Many modifications and variations are possible in light of the above teachings. It is, therefore, to be understood that within the scope of the appended claims, the invention may be practiced otherwise than using the example embodiments which have been specifically described. For that reason the following claims should be studied to determine the true scope and content of this invention.

What is claimed is:

1. A computed tomography scanner comprising:
   an x-ray source that generates x-rays;
   an x-ray detector mounted opposite the x-ray source;
   a base;
   a rocking beam pivotally attached to the base about a rocking beam axis, wherein the rocking beam includes a first end and an opposing second end;
   a first wheel connected to the rocking beam between the rocking beam axis and the first end; and
   a second wheel connected to the rocking beam between the rocking beam axis and the opposing second end.

2. The computed tomography scanner as recited in claim 1 further including a gantry including a first arm and a second arm, wherein the first arm houses the x-ray source and the second arm houses the x-ray detector and the gantry rotates about a gantry axis that is substantially horizontal.

3. The computed tomography scanner as recited in claim 1 wherein the x-ray source is a cone-beam x-ray source.

4. The computed tomography scanner as recited in claim 1 wherein the base includes a front area and a rear area and the rocking beam is pivotally attached to the front area of the base.

5. The computed tomography scanner as recited in claim 4 further including a third wheel and a fourth wheel each connected near the rear area of the base.

6. The computed tomography scanner as recited in claim 5 wherein the third wheel and the fourth wheel are fixed relative to the base in at least a generally vertical direction.

7. The computed tomography scanner as recited in claim 1 wherein the rocking beam is substantially horizontal when the computed tomography scanner is located on a level floor.

8. The computed tomography scanner as recited in claim 1 wherein the rocking beam pivots about the rocking beam axis to raise the first end of the rocking beam and the first wheel relative to the base and to lower the opposing second end of the rocking beam and the second wheel relative to the base.

9. The computed tomography scanner as recited in claim 1 further including a pivot post connected to the rocking beam and rotatable about the rocking beam axis, wherein rotation of the pivot post rotates the rocking beam about the rocking beam axis.

10. The computed tomography scanner as recited in claim 1 further including a flange that extends transversely from the base, wherein at least one bumper is mounted on the flange and is located between the flange and an upper surface of the rocking beam.

11. The computed tomography scanner as recited in claim 10 wherein the at least one bumper comprises a first bumper and a second bumper, and the first bumper is located between the first end of the rocking beam and the rocking beam axis and the second bumper is located between the opposing second end of the rocking beam and the rocking beam axis.

12. The computed tomography scanner as recited in claim 10 wherein the at least one bumper is made of rubber.

13. A computed tomography scanner comprising:
    an x-ray source that generates x-rays;
    an x-ray detector mounted opposite the x-ray source;
    a base including a front area and a rear area;
    a rocking beam pivotally attached to the front area of the base about a rocking beam axis, wherein the rocking beam includes a first end and an opposing second end;
    a first wheel connected to the rocking beam between the rocking beam axis and the first end;
    a second wheel connected to the rocking beam between the rocking beam axis and the opposing second end; and
    a third wheel and a fourth wheel each connected near the rear area of the base, wherein the third wheel and the fourth wheel are fixed relative to the base in at least a generally vertical direction, wherein the rocking beam pivots about the rocking beam axis to raise the first end of the rocking beam and the first wheel relative to the base and to lower the opposing second end of the rocking beam and the second wheel relative to the base.

14. The computed tomography scanner as recited in claim 13 wherein the rocking beam is substantially horizontal when the computed tomography scanner is located on a level floor.

15. The computed tomography scanner as recited in claim 13 further including a pivot post connected to the rocking beam and rotatable about the rocking beam axis, wherein rotation of the pivot post rotates the rocking beam about the rocking beam axis.

16. The computed tomography scanner as recited in claim 13 further including a flange that extends transversely from the base, wherein a first bumper and a second bumper are mounted on the flange, and the first bumper is located between the first end of the rocking beam and the rocking beam axis and the second bumper is located between the opposing second end of the rocking beam and the rocking beam axis.

17. A method for stabilizing a position of a computed tomography scanner, the method comprising the steps of:
   positioning the computed tomography scanner including a base on a floor with an unlevel portion; and
   raising a first wheel relative to the base and lowering a second wheel relative to the base to stabilize the computed tomography scanner.

18. The method as recited in claim 17 wherein the step of raising the first wheel and lower the second wheel including pivoting a rocking beam about a rocking beam axis relative to the base, wherein the first wheel is connected to the rocking beam between the rocking beam axis and a first end of the rocking beam and the second wheel is connected to the rocking beam between the rocking beam axis and an opposing second end of the rocking beam.

19. The method as recited in claim 17 further including the steps of:
   positioning a body part between an x-ray source and an x-ray detector;
   revolving the x-ray source and the x-ray detector about the body part;
   taking a series of images from the x-ray detector from a plurality of positions about the body part during the step of revolving; and
   generating a three-dimensional model of the body part from the series of images.

20. The computed tomography scanner as recited in claim 1 wherein the base is stationary during a CT scan.

21. The computed tomography scanner as recited in claim 2 wherein the first arm and the second arm are substantially parallel.

22. The computed tomography scanner as recited in claim 13 wherein the base is stationary during a CT scan.

23. The computed tomography scanner as recited in claim 13 wherein a first arm houses the x-ray source and a second arm houses the x-ray source, and the first arm and the second arm are substantially parallel.

24. The method as recited in claim 17 including the step of retaining the base on the floor at a stationary position during a CT scan.

* * * * *

UNITED STATES PATENT AND TRADEMARK OFFICE
CERTIFICATE OF CORRECTION

PATENT NO. : 7,422,368 B2  Page 1 of 1
APPLICATION NO. : 11/546933
DATED : September 9, 2008
INVENTOR(S) : Stayman et al.

It is certified that error appears in the above-identified patent and that said Letters Patent is hereby corrected as shown below:

ON THE TITLE PAGE:

Item [75] Inventor Teofilovic's information should read as follows: --Dejan Teofilovic, Ann Arbor, MI (US)--

Signed and Sealed this

Fourth Day of November, 2008

JON W. DUDAS
*Director of the United States Patent and Trademark Office*